(12) United States Patent
Wang et al.

(10) Patent No.: US 9,131,857 B2
(45) Date of Patent: Sep. 15, 2015

(54) APPARATUS AND METHOD FOR BATTERY-FREE BLOOD PRESSURE MONITOR

(75) Inventors: Tianren Wang, Raleigh, NC (US); Xuyao Shi, Raleigh, NC (US); Siwen Liu, Raleigh, NC (US); Wenjiao Wang, Raleigh, NC (US)

(73) Assignee: Tianren Wang, Santa Clara, CA (US)

( * ) Notice: Subject to any disclaimer, the term of this patent is extended or adjusted under 35 U.S.C. 154(b) by 805 days.

(21) Appl. No.: 13/372,461

(22) Filed: Feb. 13, 2012

(65) Prior Publication Data

US 2013/0211267 A1   Aug. 15, 2013

(51) Int. Cl.
*A61B 5/021* (2006.01)

(52) U.S. Cl.
CPC .................................. *A61B 5/02141* (2013.01)

(58) Field of Classification Search
CPC ............................. A61B 5/02141; A61B 5/021
USPC ................. 600/479, 480, 490–496, 498–503; 606/202, 203
See application file for complete search history.

(56) References Cited

U.S. PATENT DOCUMENTS

| | | | | |
|---|---|---|---|---|
| 1,953,466 | A * | 4/1934 | Corwin | 600/490 |
| 5,540,231 | A * | 7/1996 | Moy | 600/490 |
| 6,293,771 | B1 * | 9/2001 | Haney et al. | 417/374 |
| 2008/0319329 | A1 | 12/2008 | Tseng | |
| 2011/0245696 | A1 | 10/2011 | Yamashita et al. | |

* cited by examiner

*Primary Examiner* — Michael Kahelin
*Assistant Examiner* — Tho Tran
(74) *Attorney, Agent, or Firm* — Jason J. Su

(57) ABSTRACT

A battery-free electronic blood pressure measuring apparatus comprising a cuff (40), an airbag (22) to push air into the cuff (40), a power generation unit which has a generator (42) and an operating handle (28) coupled with the wall of the airbag (22) to generate electrical power, and a display device (44) to receive electrical power from the power generation unit, detect a blood pressure signal from the cuff (40), generate and display a blood pressure measurement. A method for electronically measuring blood pressure with a battery-free sphygmomanometer comprises pressing an airbag and a generator-driving structure attached to the airbag wall, which leads to electrical power generation and cuff inflation by the airbag at the same time, and measuring the blood pressure with the generated electrical power.

1 Claim, 25 Drawing Sheets

APPARATUS AND METHOD FOR BATTERY-FREE BLOOD PRESSURE MONITOR

CROSS-REFERENCE TO RELATED APPLICATIONS

Not Applicable

STATEMENT REGARDING FEDERALLY SPONSORED RESEARCH OR DEVELOPMENT

Not Applicable

SEQUENCE LISTING OR PROGRAM

Not Applicable

BACKGROUND OF THE INVENTION

1. Field of Invention

The present invention relates to an electronic blood pressure measuring apparatus, particularly to a manual driven electronic blood pressure measuring apparatus.

2. Prior Art

Sphygmomanometers, or blood pressure monitors, have been used for many years as tools for measuring blood pressure values. The typical sphygmomanometer has an arm-banding cuff inflated by an airbag (i.e. an inflation bulb) to restrict blood flow in an artery vessel of a living body, as well as a mercury or mechanical manometer to measure the arterial blood pressure. It is usually used in conjunction with a means such as a stethoscope to determine the systolic and diastolic pressure. The old fashioned mechanical blood pressure monitor normally has to be operated by an experienced health care provider.

With the ongoing global epidemic of cardiovascular disease, blood pressure monitoring is very important from the perspective of health care. Due to their ease of operation and relative measurement accuracy, electronic versions of sphygmomanometers are becoming widely adopted for use at home as well as in hospitals.

Electronic blood pressure monitors, whether automatic or semi-automatic, require an external electric power source to operate, such as a dry cell battery or an AC power supply. However, the external power supply requirement cannot be always readily met under many urgent circumstances, such as in post-disaster emergency situations, or simply in many outdoor environments where a dead battery cannot be supplemented with an AC power backup source. Human life may be threatened in these circumstances.

Several types of self power-generating blood pressure monitors have been proposed, for example, the U.S. patent applications 2008/0319329A1 (2007) of Tseng and 2011/0245696A1 (2011) of Yamashita et al. Although they provide different ways to tackle the issue, there are some obvious problems with each of them. For example, Tseng's patent application harnesses the pressurized air from the elastic bulb to generate the necessary electric power. Disadvantageously, this approach requires a considerable amount of control equipment for generating electricity from air pressure. Yamashita et al. discloses a solar panel that may be used to generate electrical power, but disadvantageously, the measurement cannot start without an initial charging process, which could be an unacceptable limitation in some urgent situations.

Therefore, there exists a great need for a convenient blood pressure monitoring device which is ready in every situation to measure this important vitality index of human beings.

SUMMARY OF THE INVENTION

The present inventor has discovered that the movement of the wall of the sphygmomanometer airbag during the deformation-restoration cycle can be operably coupled to generate sufficient electrical power for blood pressure monitoring. In accordance with the invention, the generation of the electrical power necessary for measuring and displaying blood pressure can be coupled to the deformation of the elastic airbag (i.e. moving of the wall of the elastic airbag). Consequently, no waiting period is required and sufficient electrical power is generated with just a few strokes of pressing the airbag, which in turn eliminates the need for any battery, high-efficiency miniature wind powered or solar powered generators or other auxiliary power sources.

The blood pressure monitor can have any desired structural means for moving with the outer surface of the airbag, which is then coupled to a generator (i.e. generator) for electrical power generation for the measurement. An operating handle has been tested to be most advantageous, however.

In other embodiments of the invention, the blood pressure monitor may have any desired structural means for moving with the inner face of wall of the airbag, which is driving a generator for electrical power generation. The inside structural means may be partially or totally enclosed in the airbag. In particular embodiments, the structural means and the generator are located inside of the airbag, resulting in a blood pressure monitor that is much more compact than the prior art.

In other embodiments according to the invention, the blood pressure monitor may have a liquid crystal display device or a set of transmitting, receiving, and display devices to display/monitor the BP measurement of the living body. Each of these details provides particular advantages and can be implemented independently of the others.

The deformation of the airbag (i.e. moving of the wall of the airbag) can be induced by an action of a limb of a human body or an external mechanical device via squeezing, clenching, or squashing. In particular embodiments of the invention, the outside structural means may be adapted for a part of a human foot to fit in, making the measuring process more convenient for people with disabled hands.

If desired, the deformation of the airbag can be switched for power generation. The electrical power generated can then be used to inflate the arm-banding cuff, as well as measure and display the blood pressure.

In particular embodiments of the invention, power storage devices may be included to store the electrical power generated by the generator and voltage regulators may be used to provide constant voltage output for other devices.

Other aspects and advantages of the invention will be apparent from the following description and the appended claims.

DETAILED DESCRIPTION

Figure 1:
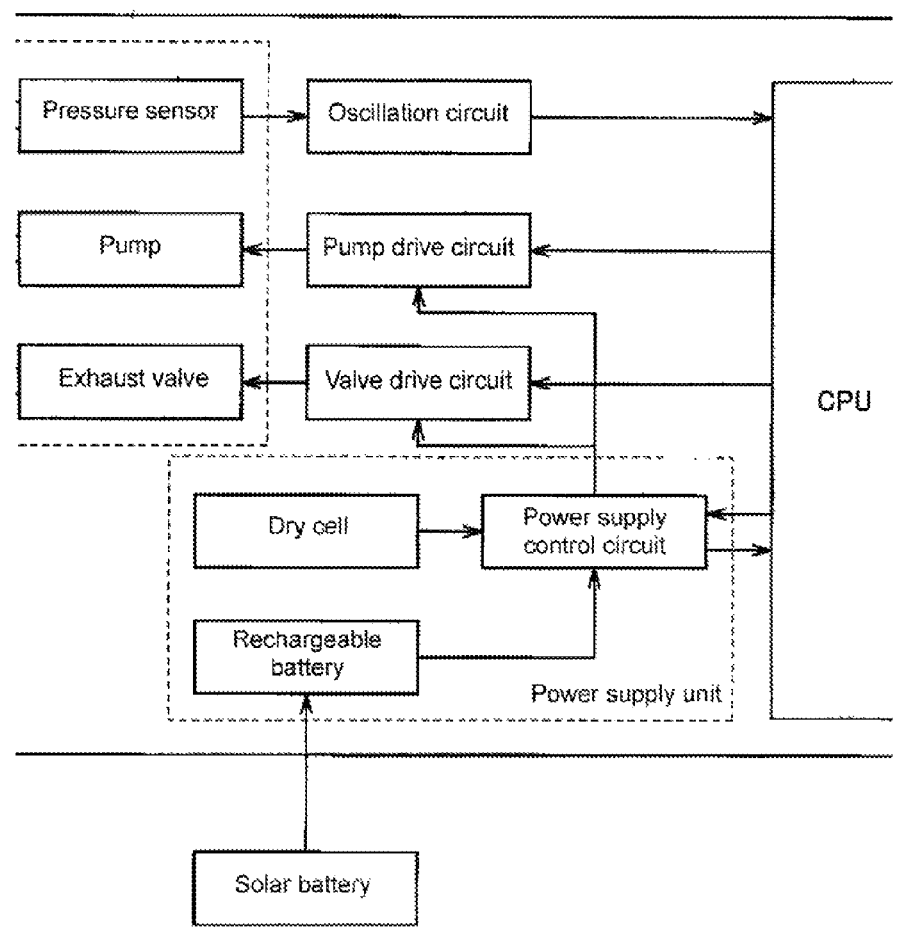
FIG. 1 shows a schematic of a type of blood pressure monitor with electrical power generation known in the prior art.
Figure 2:
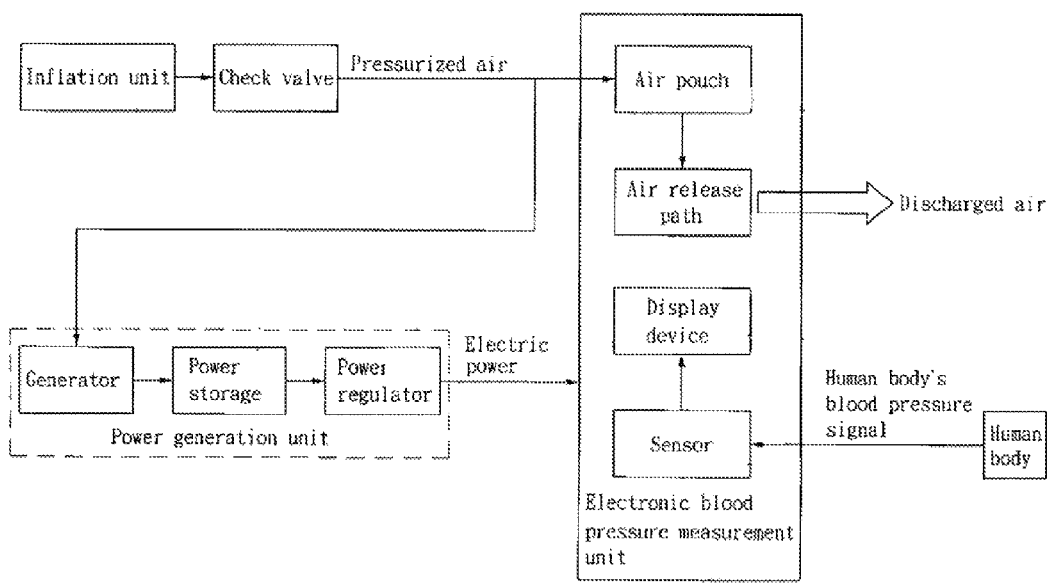
FIG. 2 shows a schematic of another type of blood pressure monitor with electrical power generation known in the prior art.

Among those known in the prior art shown in FIGS. 1 and 2 are the blood pressure (BP) monitors or sphygmomanometers with electrical power generation ability. The FIG. 1 device comprises a solar battery and a rechargeable battery to provide electrical power to drive various parts of the sphygmomanometer. The FIG. 2 device comprises a generator which uses the pumped pressurized air to generate electrical power for BP measurement and display.

The known BP measuring devices with electrical power generation ability are not operable for immediate BP measuring without a charging process, which could be problematic due to inhospitable weather conditions (especially for the device in FIG. 1) or could be rather strenuous on the operator due to the questionable efficiency of the process (especially for the device in FIG. 2). Additionally, it could take a period of waiting time from a few minutes to a few hours to produce enough electricity. The present inventors recognized that enabling the BP measuring device to be immediately operable would provide tremendous benefits, as detailed herein above. Indeed, in order to quicken the charging process, the solar panel in FIG. 1 and the pressurized air generator in FIG. 2 are expected to be too large to be easily portable.

FIGS. 3-13

The First Embodiment

The present inventor has recognized that the movement of the wall of the inflation bulb (or airbag) could be coupled with an operating bar to generate enough electricity to power the blood pressure monitor and inflate the cuff. In accordance with the invention, the blood pressure monitor can have any desired structural means for moving with the wall of the airbag, which is then coupled to a generator for electrical power generation for measurement. An operating handle has been tested to be advantageous for this purpose.

In this way, no waiting period is needed and enough electrical power is generated with a few strokes of pressing the airbag, which in turn eliminates the involvement of any battery or miniature wind or solar powered generator.

Figure 3:
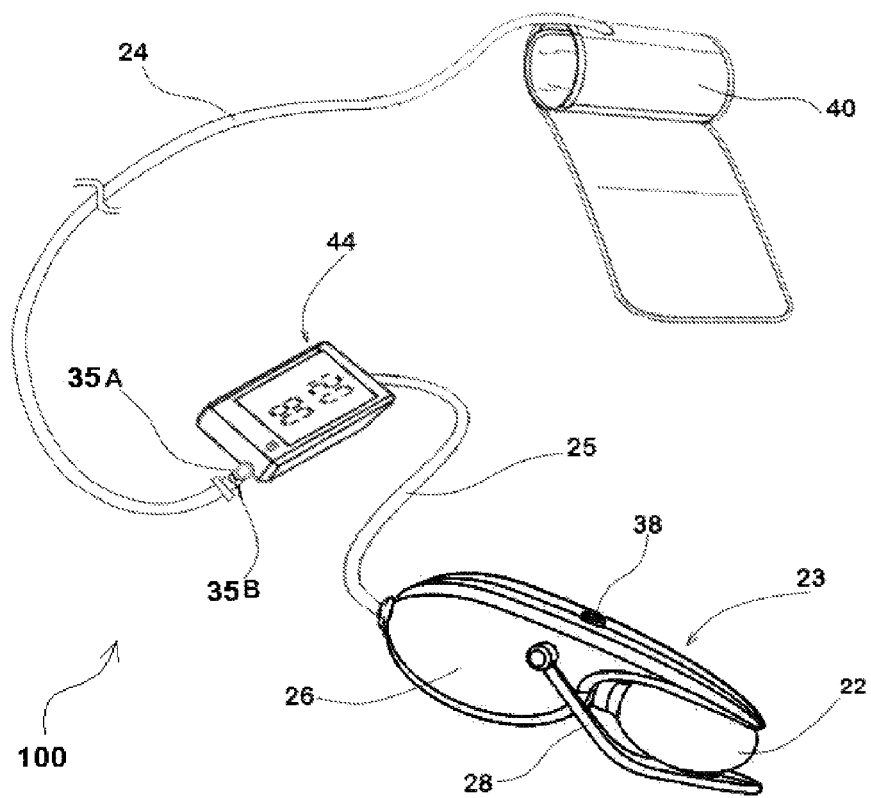
FIG. 3 shows a schematic of an overall configuration of a blood pressure monitor according to the first embodiment of the present invention.

FIG. 3 illustrates a battery-free electronic BP measuring and displaying device, referred to as a BP monitor 100 in a first embodiment of the present invention.

The electronic BP monitor 100 in FIG. 3 comprises a main body made up of a display device 44 and an inflation-power unit 23 being joined through a first rubber tube 25, and a cuff 40 to be applied to an arm (omitted from the drawing) and connected with the main body by a second rubber tube 24. The cuff 40 refers to a band-shaped structure that has a bladder and can be wrapped around a part of the living body. The second rubber tube 24 has a tube adaptor 35B at one end for plugging into an outlet 35A on the display device 44.

Figure 4:
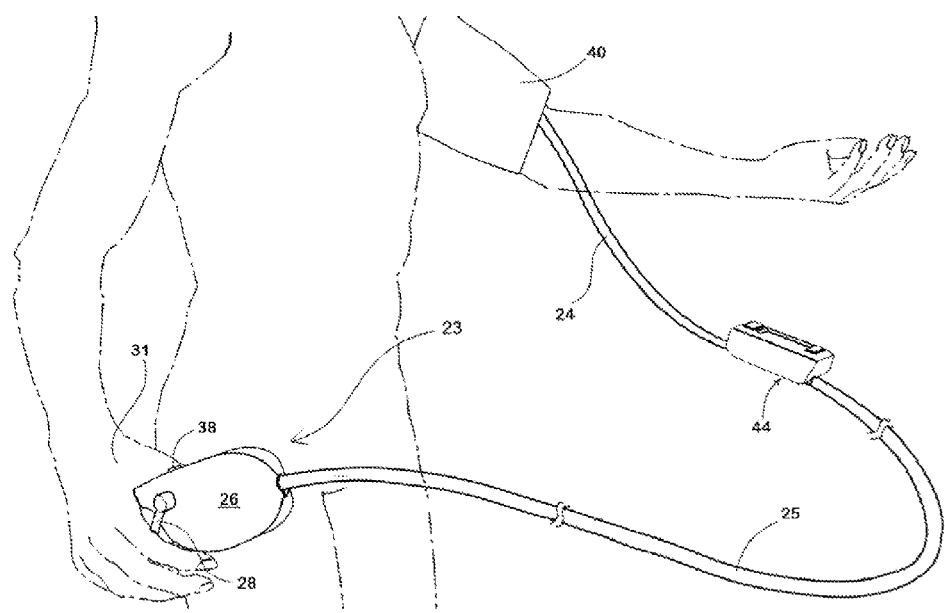
FIG. 4 is a diagram illustrating usage of the blood pressure monitor according to the first embodiment of the present invention.

As illustrated in FIG. 4, the cuff 40 can be wrapped around one upper arm of a patient while the inflation-power unit 23 can be conveniently within reach of the patient's hand 31. A wire (omitted in the drawings) is mounted on the first rubber tube 25 to conduct the generated electrical power from the inflation-power unit 23 to the display device 44.

The external configuration of the inflation-power unit 23 of the electronic BP monitor 100 of FIG. 3 is illustrated in FIGS. 5-8. FIGS. 5A-B are close-up drawings showing the inflation-power unit 23 being held by the hand 31. FIG. 6A shows the side view of the inflation-power unit 23, while FIG. 6B shows the sectional side view. FIG. 8C shows a rearward angular view of the inflation-power unit 23 from the top.

Figure 6A:
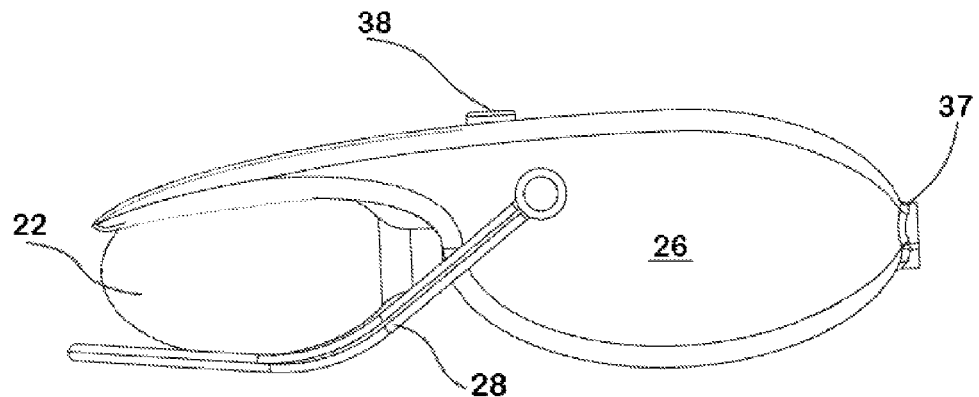
FIG. 6A illustrates a side view of the inflation-power unit portion of the blood pressure monitor according to the first embodiment of the present invention.
Figure 6B:
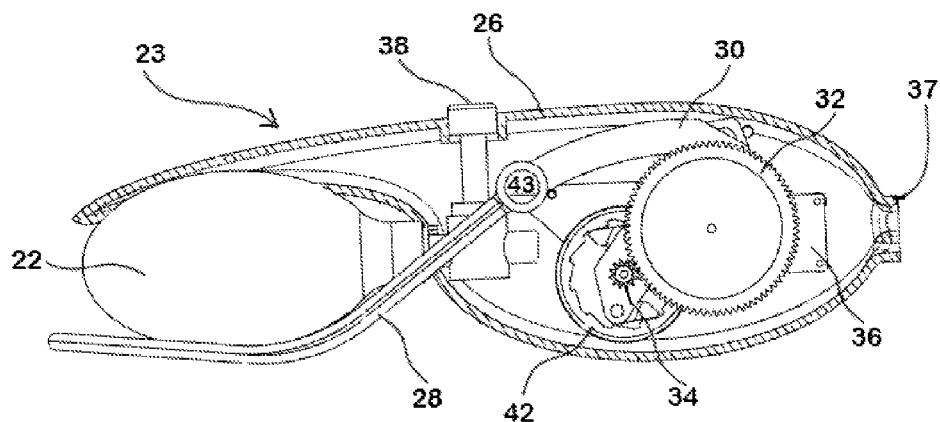
FIG. 6B illustrates a sectional side view of the inflation-power unit portion of the blood pressure monitor according to the first embodiment of the present invention.
Figure 7A:
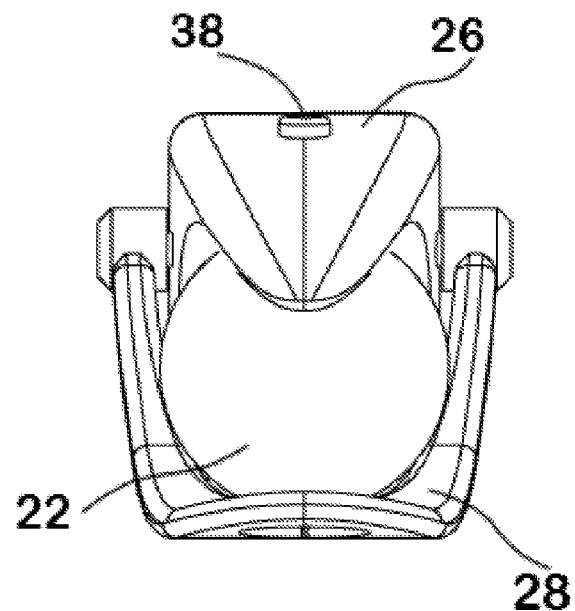
FIG. 7A illustrates a rear view of the inflation-power unit portion of the blood pressure monitor according to the first embodiment of the present invention.
Figure 7B:
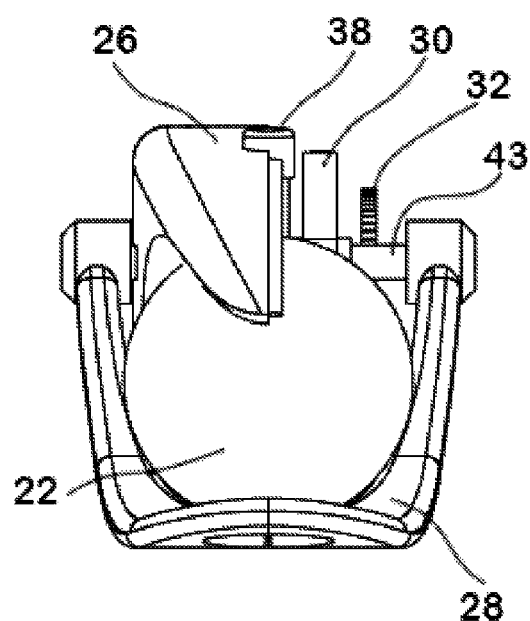
FIG. 7B illustrates a rear view of a partially open state of the inflation-power unit portion of the blood pressure monitor according to the first embodiment of the present invention.
Figure 7C:
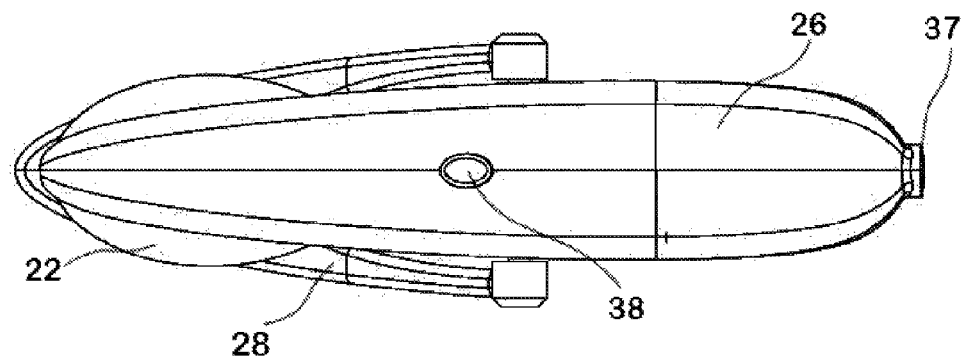
FIG. 7C illustrates a top view of the inflation-power unit portion of the blood pressure monitor according to the first embodiment of the present invention.
Figure 7D:
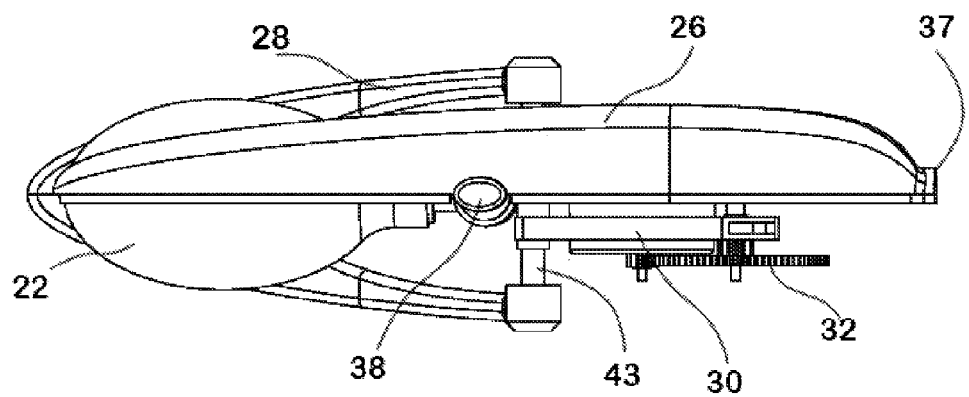
FIG. 7D illustrates a top view of a partially open state of the inflation-power unit portion of the blood pressure monitor according to the first embodiment of the present invention.
Figure 7E:
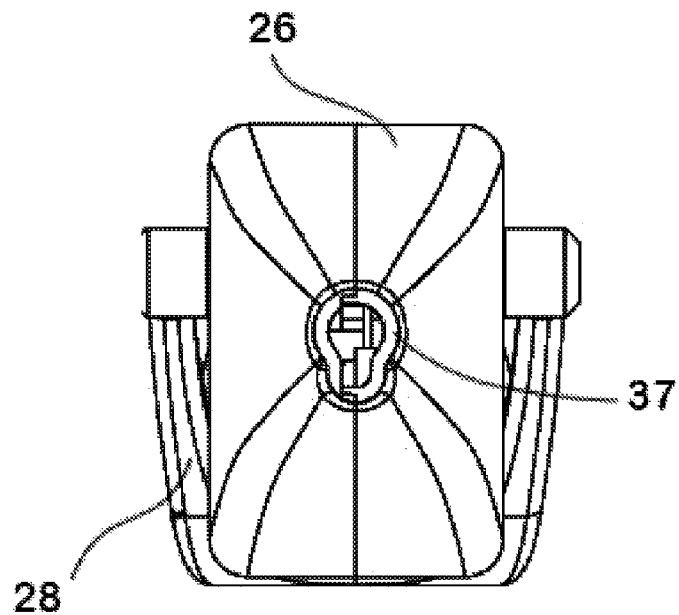
FIG. 7E illustrates a front view of the inflation-power unit portion of the blood pressure monitor according to the first embodiment of the present invention.
Figure 7F:
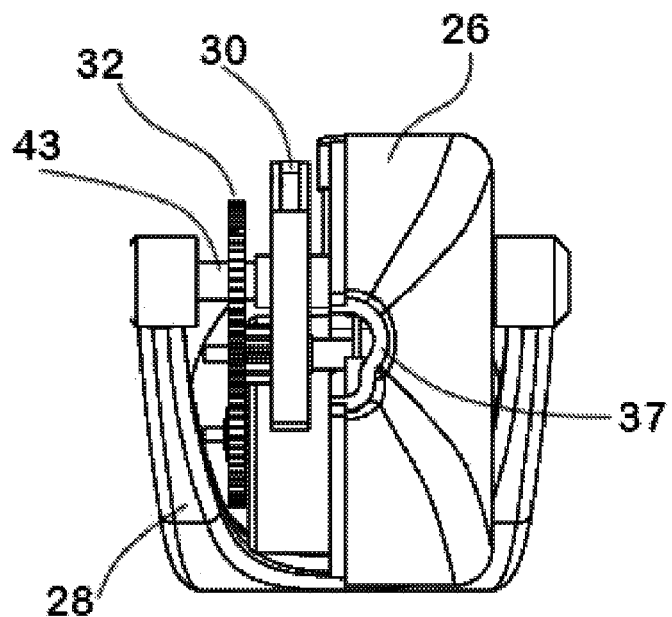
FIG. 7F illustrates a front view of a partially open state of the inflation-power unit portion of the blood pressure monitor according to the first embodiment of the present invention.

As shown in FIG. 6B, the inflation-power unit 23 of the electronic BP monitor 100 comprises a casing 26, an airbag 22 to inflate the cuff 40, an air-conducting unit to conduct the air between the airbag 22 and the cuff 40, an operating handle 28 pairing with part of the casing 26 to confine the airbag 22, a tooth-bearing rack 30 pivotally connected with the operating handle 28 via a fulcrum shaft 43, a double gear 32 to connect with the tooth-bearing rack 30, a generator (i.e. an electrical generator) 42 driven by the double gear 32, and a generator circuit 36 fixed on the inner face of casing 26 to process the electrical current from the generator 42.

Four parts of the external configuration of the inflation-power unit 23 can be seen in FIGS. 5-8, including the casing 26, the operating handle 28, the airbag 22 securely housed in the socket between the casing 26 and the operating handle 28, and the upper part of the air-releasing valve 38. The casing 26 has a shape like a tadpole, which has a head and a tapering tail. The head of the casing 26 is housing the generator 42 and many other pieces as depicted in FIG. 6B. On the tip of the head of the casing 26 is an air outlet 37, which is connected with the first rubber tuber 25 to conduct the air through the inflation-power unit 23. The tapering tail of the casing 26 has an outer face towards the palm of the hand 31 and an inner face towards the upper part of the airbag 22. The inner face of the tapering tail of casing 26 has a configuration to hold the airbag 22, in order to be used as a supporting base for the airbag 22 during inflation. The operating handle 28 is under the lower part of the airbag 22 and pairs with the tail of the casing 26 to confine the airbag. The operating handle 28 is a forklike structure having two ends: one end is bifurcated and pivotally connected to the casing 26 with the fulcrum shaft 43 while the other end is tapered off and configured to hold the lower part of the airbag 22. The operating handle 28 can pivotally move up and down during the inflation and electricity generation process.

The top part of the air releasing valve 38 is in the middle part of the casing 26 and vertically right above the outlet of the airbag 22, so it can be conveniently controlled by the holding hand 31. When being pressed, the air can be released through the air releasing valve 38.

The internal configuration of the inflation-power unit 23 of the electronic BP monitor will be explained mainly based on FIGS. 6B, 8B and 9A-B.

The tooth-bearing rack 30, the double gear 32, the generator 42, and the air-conducting unit are mounted in the casing 26. The air-conducting unit comprises an air-releasing valve 38 to manually release the air during the BP measurement, the air outlet 37 on the case 26 to connect with the first rubber tube 25, and an air-conducting tube (omitted in the drawings) connecting the air-releasing valve 38 and the air outlet 37. Because of the air-conducting tube being included, the casing 26 doesn't have to be airtight.

Figure 8A:
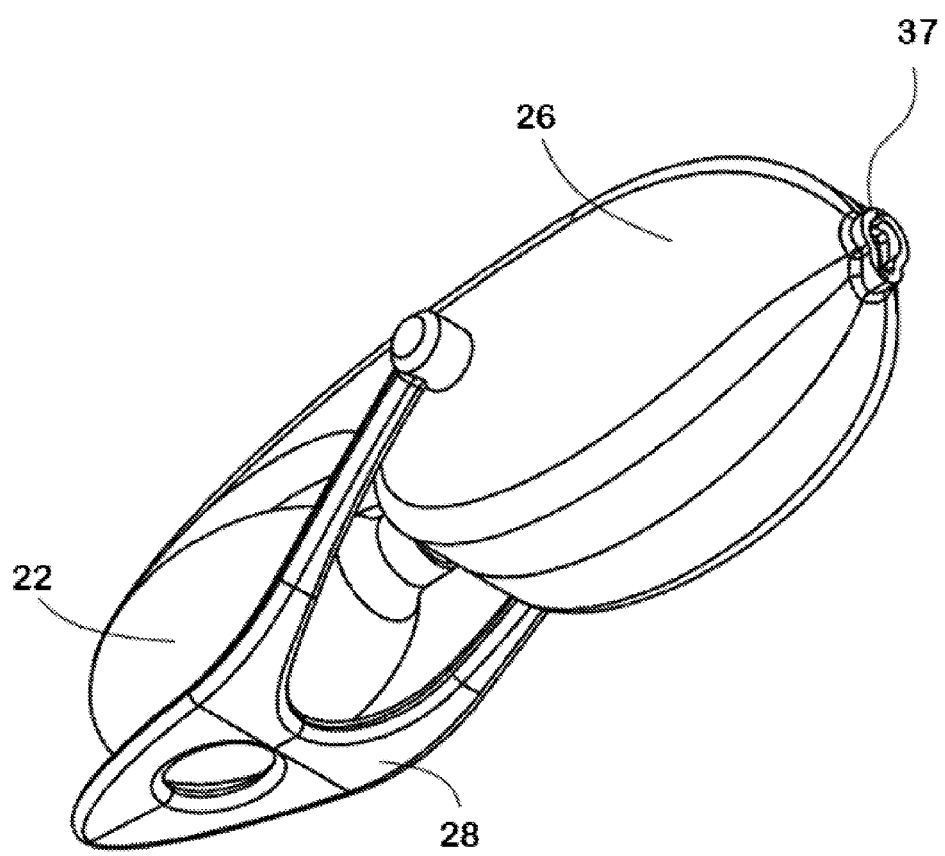
FIG. 8A illustrates a bottom frontal view of the inflation-power unit portion of the blood pressure monitor according to the first embodiment of the present invention.
Figure 8B:
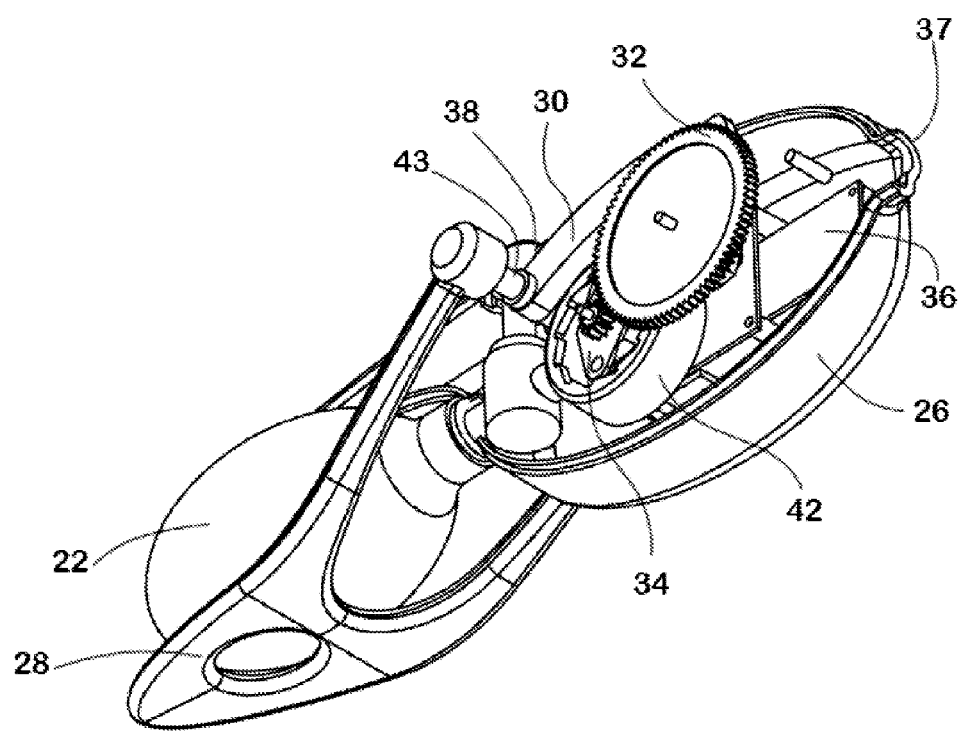
FIG. 8B illustrates a bottom frontal view of a partially open state of the inflation-power unit portion of the blood pressure monitor according to the first embodiment of the present invention.
Figure 8C:
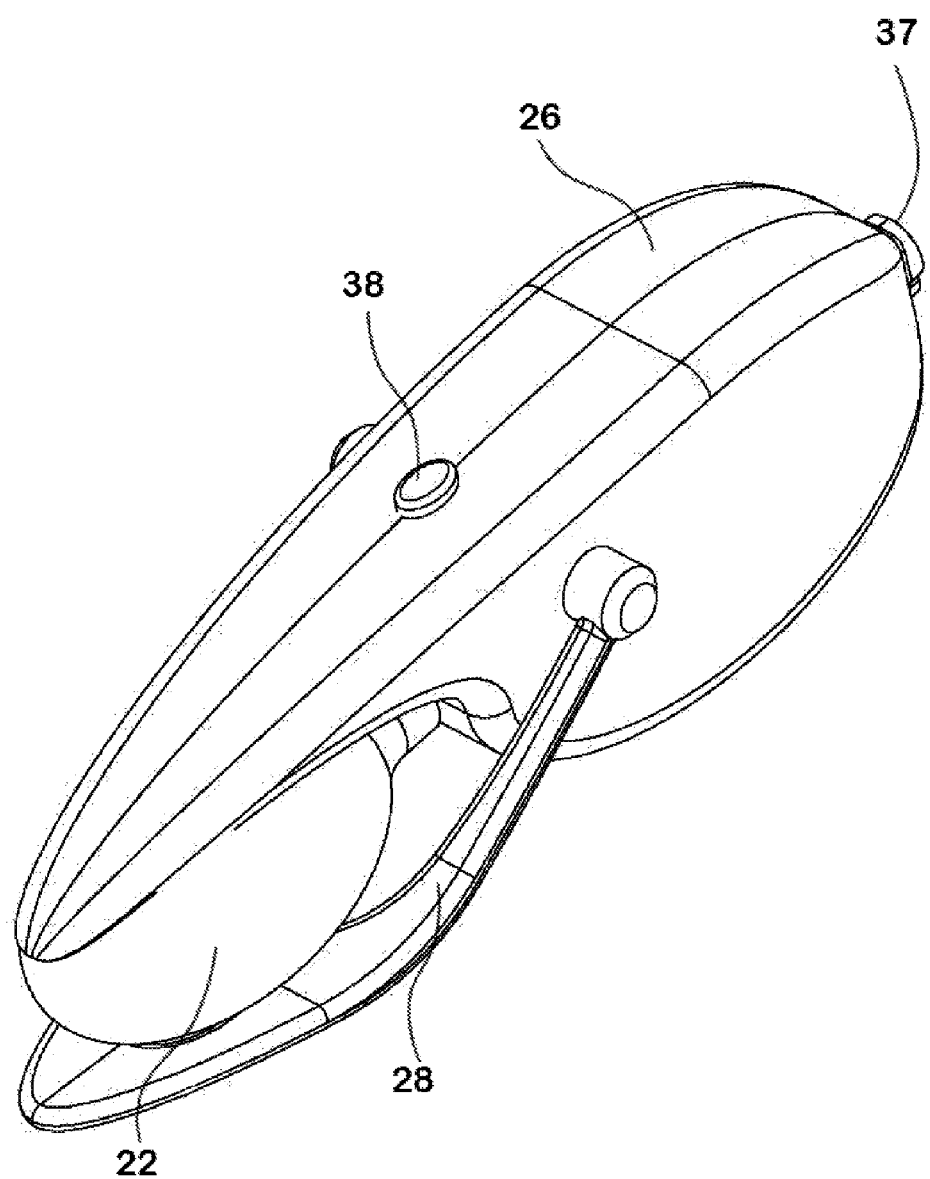
FIG. 8C illustrates a top rearward view of the inflation-power unit portion of the blood pressure monitor according to the first embodiment of the present invention.
Figure 8D:
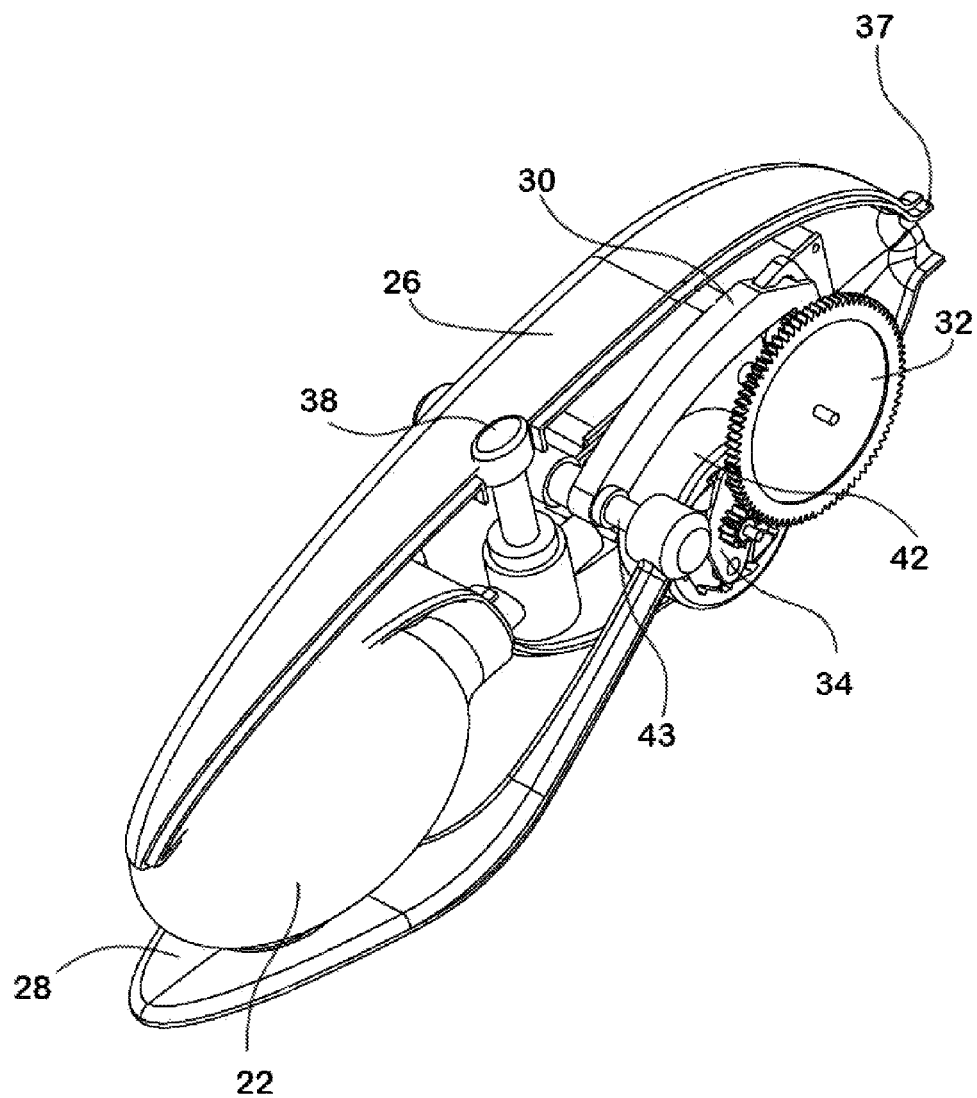
FIG. 8D illustrates a top rearward view of a partially open state of the inflation-power unit portion of the blood pressure monitor according to the first embodiment of the present invention.
Figure 9A:
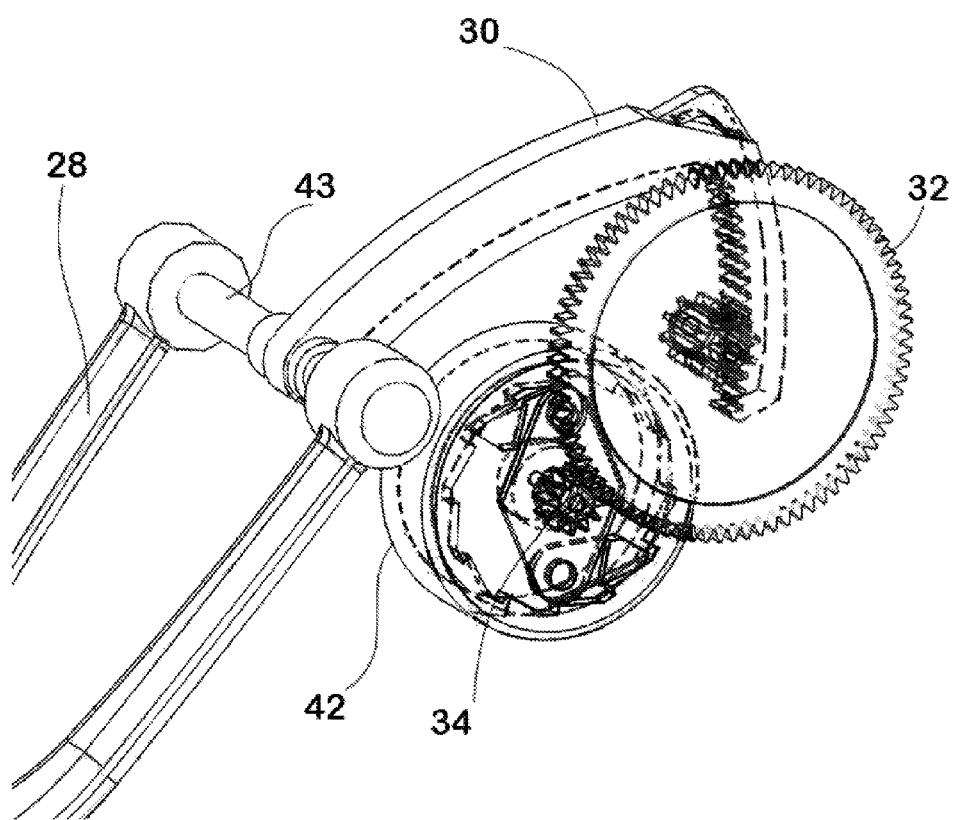
FIG. 9A illustrates a close-up perspective view of a gearing system of the blood pressure monitor according to one or more embodiments of the present invention.
Figure 9B:
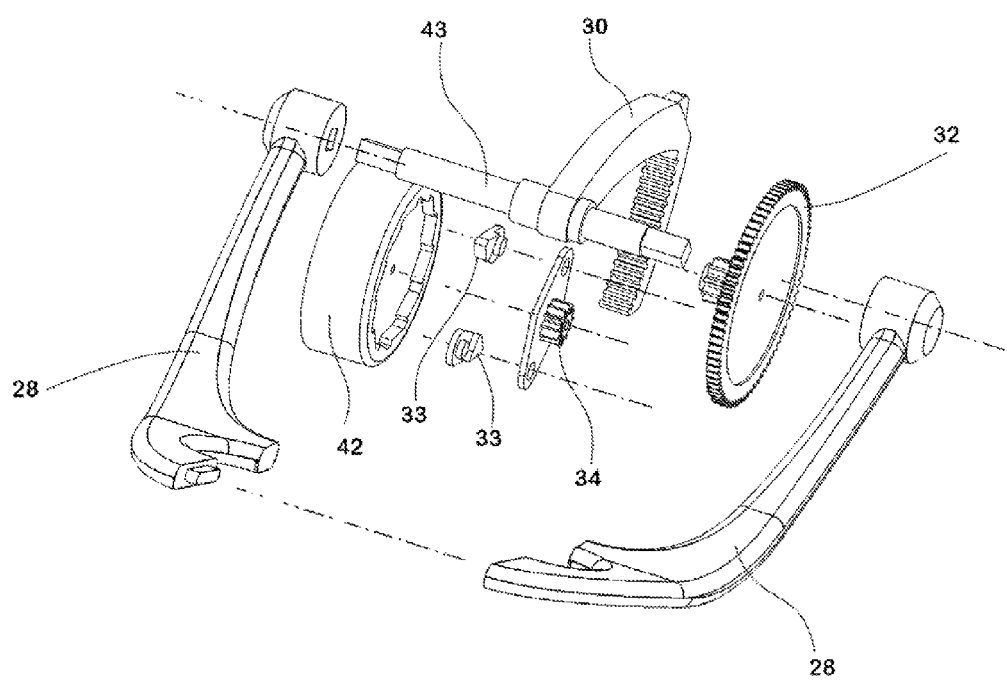
FIG. 9B illustrates an exploded view of the gearing system of the blood pressure monitor according to one or more embodiments of the present invention.

As shown in FIGS. 8D, and 9A-B, the fulcrum shaft 43 works as a docking site for the operating handle 28 and the tooth-bearing rack 30. Both the operating handle 28 and the tooth-bearing rack 30 are fixed to the fulcrum shaft 43, therefore being able to move up and down with rotation of the fulcrum shaft 43. The fulcrum shaft 43 is fixed through the casing 26. The tooth-bearing rack 30 is a structure taking a general shape of the number "7" and has two ends, where one end is the stalk of the number "7" which is fixed on the fulcrum shaft 43 while the other end is the top beam part of the number "7" which is placed vertically and has a plurality of teeth meshing with the teeth on the small diameter portion (i.e., pinion) of the double gear 32. Therefore, when the tooth-bearing rack 30 moves with the rotation of the fulcrum shaft 43, the tooth-bearing rack 30 drives the rotation of the double gear 32 and makes the teeth on the large diameter portion of the double gear 32 rotate as well.

The teeth on the large diameter portion of the double gear 32, as shown in FIGS. 9A-B, mesh with the motor gear 34, which is driving the generator 42 to produce electricity. The motor gear 34 is connected to the generator 42 via two pieces of pawl 33. As such, the up and down movement of the operating handle 28 can be transmitted to drive rotational movement of the generator 42 for electricity generation.

The display device 44 comprises a pressure sensor (omitted in the drawings) for sensing the pressure in the cuff 40 delivered via the second rubber tube 24 and producing BP signals, a standard signal processing and display circuit (omitted from the drawings) for processing the BP signals received and generating and outputting BP values, and a liquid crystal display device (omitted from the drawings) on its surface for receiving and displaying the BP values. In this way, the display device 44 can automatically receive and process the BP signals the cuff 40 and have the systolic and diastolic BP values displayed on its surface. The pressure sensor and the standard signal processing and display circuit form a electronic blood pressure measurement unit for receiving the electrical power output from the power generation unit and processing a blood pressure signal from the cuff generating and outputting the BP values; the liquid crystal display device forms a display element for receiving and displaying the BP values. The design and installation of the display device 44 should be within the knowledge of an artisan in the trade.

In particular embodiments of the invention, power storage devices may be included to store the electrical power generated by the generator, and voltage regulators may be used to provide constant voltage output.

Figure 15:
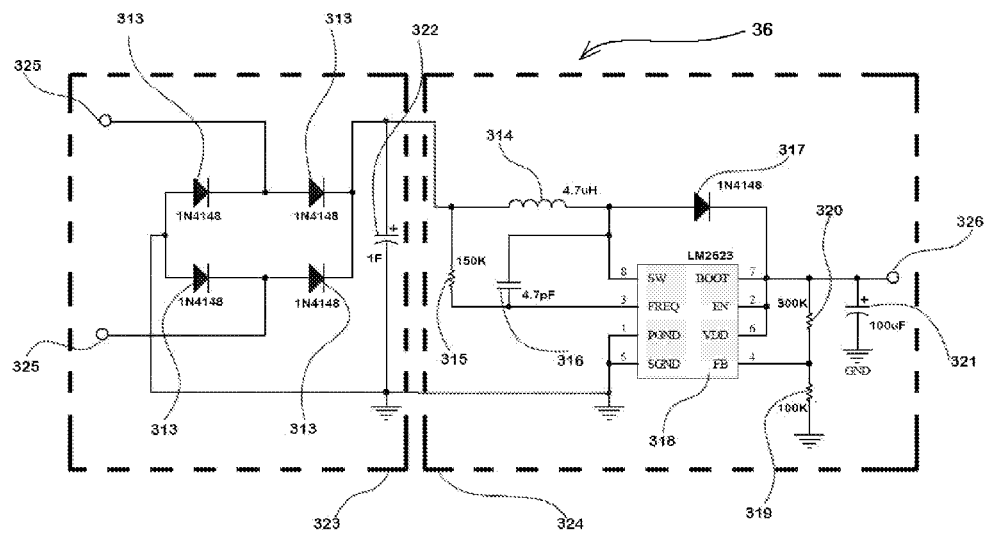
FIG. 15 is a schematic of a generator circuit according to the one or more embodiments of the present invention.

FIG. 15 is a schematic of the generator circuit 36 for the power storage and voltage regulation process. Basically, the generator circuit 36 can be divided into two parts: an AC-DC conversion unit 323, and a voltage stabilizer 324.

An electrical current 325 for the circuit is an AC power sine wave from the generator 42. The electrical current 325 first goes through a bridge rectifier which consists of four diodes 313 and is converted from AC voltage to non-linear DC voltage. Our experiments demonstrated that the maximum voltage of the electrical current 325 does not exceed the maximum voltage of the super capacitor 322. The power can then be stored in the super capacitor 322. Later the electrical current 325 is fed into a voltage stabilizer 324 which comprises an inductor 314, a resistor 315, a capacitor 316, and a DC-DC voltage converter IC 318. Other transistors can be used to replace the DC-DC voltage converter IC 318. A first resistor 319 and a second resistor 320 are used to adjust the output voltage value. A diode 317 is used to protect the circuit and a capacitor 321 is to keep the output DC voltage constant. Finally a constant DC voltage power 326 is generated and provided to the signal processing and display unit 44.

The schematic as in FIG. 15 is just one implementation according to one or more embodiments of this invention. There are many other circuits and electrical components that can achieve the same function of the process.

FIGS. 4, 5A, 10A-D, and 14

Operation

Figure 14:
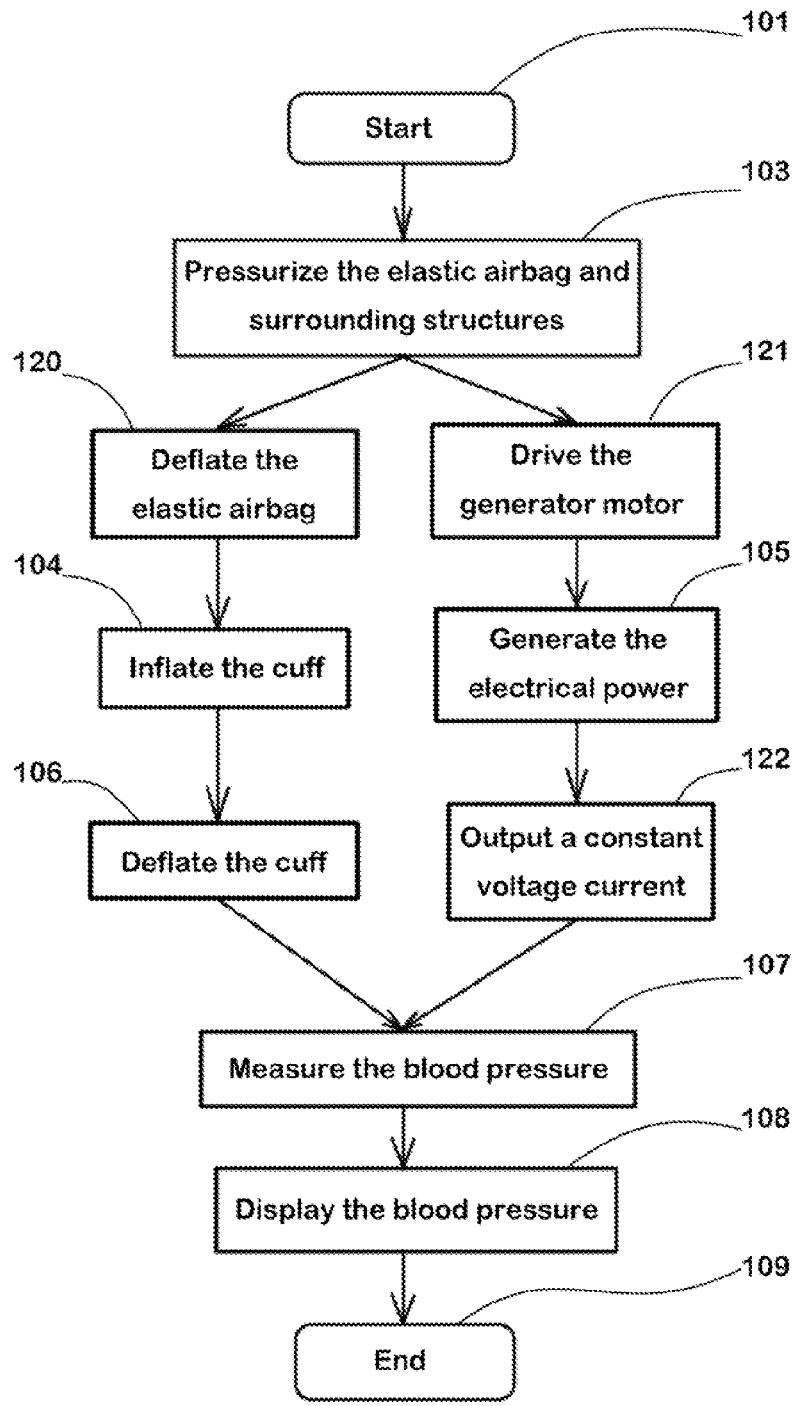
FIG. 14 is a flowchart showing blood pressure measurement-related processing, according to the one or more embodiments of the present invention.

The flowchart shown in FIG. 14 demonstrates the general flow of the process.

As shown previously in FIG. 4, in order for a user to use the electronic BP monitor the cuff 40 is first wrapped around the upper arm of the patient whose blood pressure is to be measured, and the second rubber tube 24 is securely connected to the display device 44 via the tube adaptor 35B. The user and the patient could be different human beings but it is advantageous for one or more embodiments of the current invention that it can be operated by the patient himself.

Figure 5A:
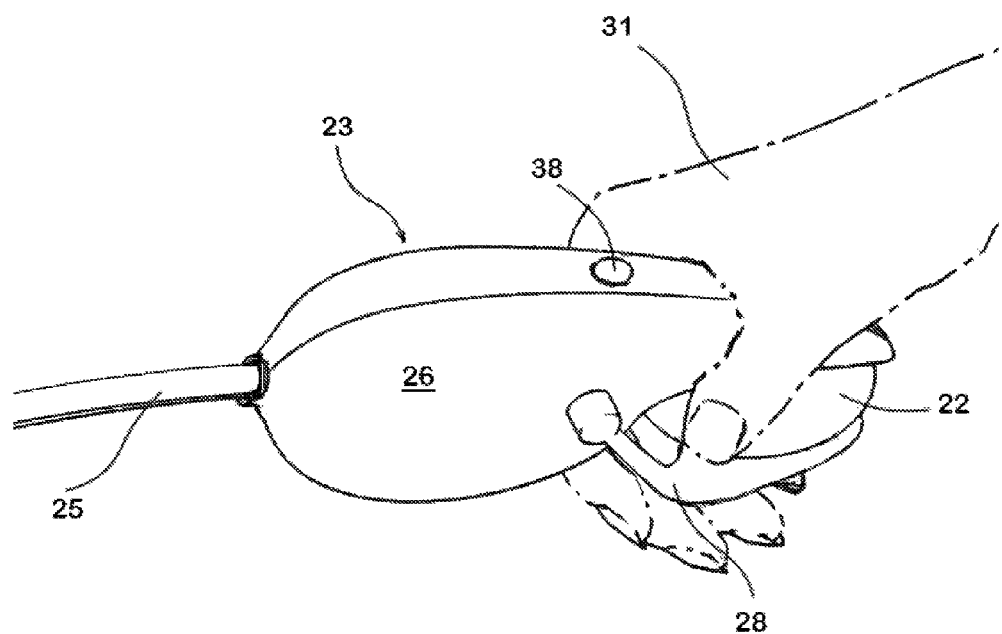
FIG. 5A illustrates a top frontal view of an inflation-power unit portion of the blood pressure monitor according to the first embodiment of the present invention.
Figure 5B:
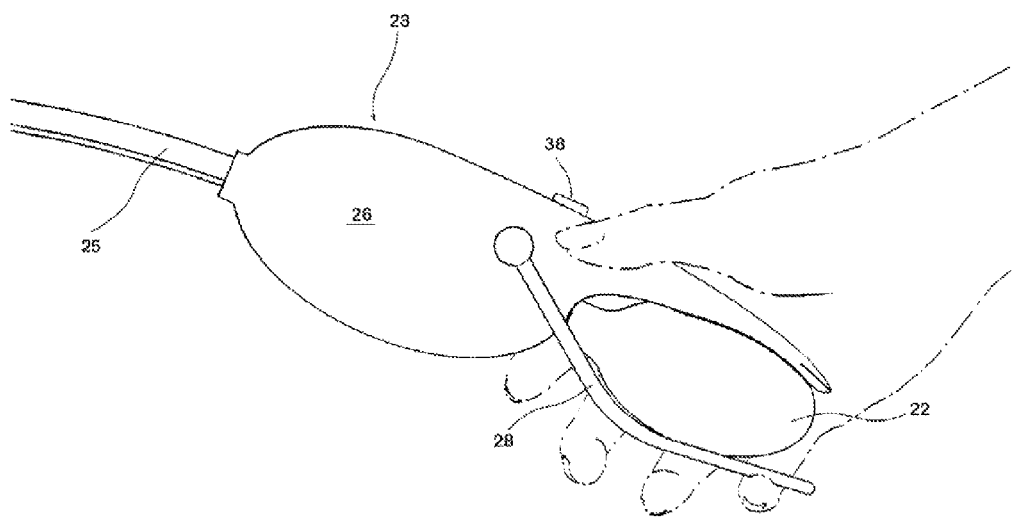
FIG. 5B illustrates a side view of the inflation-power unit portion of the blood pressure monitor according to the first embodiment of the present invention.

Next, the inflation-power unit 23 is held by the hand 31 in a preferred orientation shown in FIG. 5A. The BP measuring process is started by making the operating handle 28 pivot in the direction indicated by the arrow in FIGS. 10A and 10B (Step 103 in FIG. 14). Specifically, when the operating handle 28 is lifted up towards the airbag 22, which is sandwiched between the operating handle 28 and the tail part of the casing 26, the wall of the airbag 22 collapses inward and the air inside is pushed out of the airbag 22 as it deflates (Step 120 in FIG. 14). Through the air-conducting unit of the inflation-power unit 23, the first rubber tube 25, the display device 44, and the second rubber tube 24, the air is channeled into the cuff 40 (Step 104 in FIG. 14).

Figure 10A:
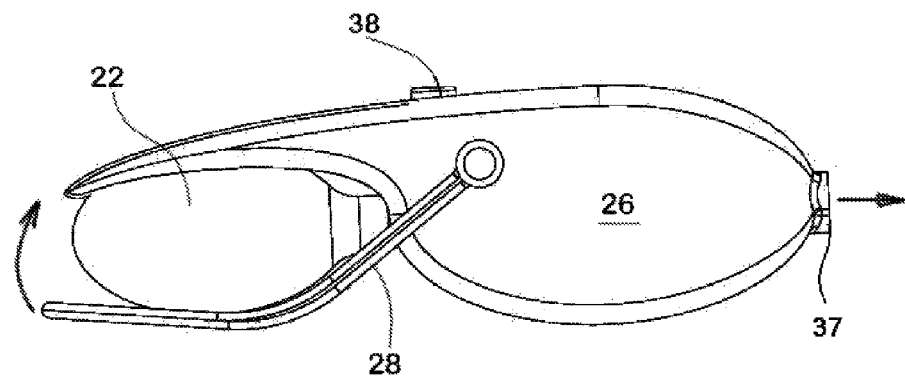
FIG. 10A illustrates a right view of the inflation-power unit portion of the blood pressure monitor according to the first embodiment of the present invention where an operating handle is moving up and an airbag is deflated.
Figure 10B:
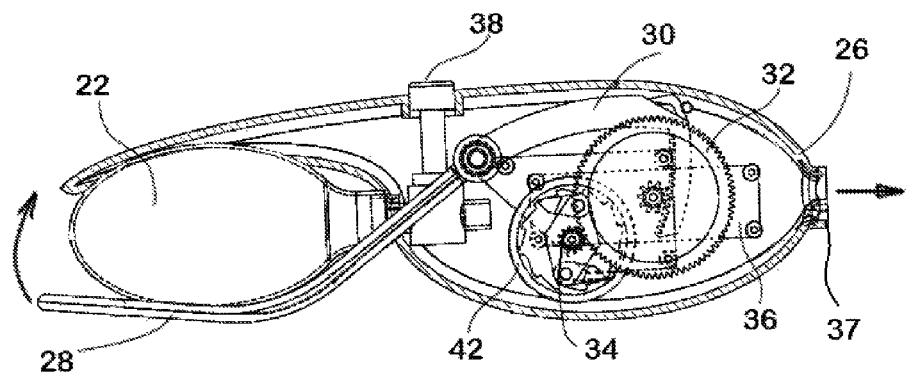
FIG. 10B illustrates a right sectional view of the inflation-power unit portion of the blood pressure monitor according to the first embodiment of the present invention where the operating handle is moving up and the airbag is deflated.

While inflating the cuff 40, the free end of the operating handle 28 swings upward around the fulcrum shaft 43 (towards the tail part of the casing 26) and pushes the part of the wall of the airbag 22 inward, as shown in FIGS. 10A and 10B (Step 121 in FIG. 14). The upward motion of the operating handle 28, about the fulcrum shaft 43, forces the tooth-bearing rack 30 to advance vertically towards the bottom part of the casing 26, driving the double gear 32 and then the motor gear 34, which operates the generator 42 by means of the two pawls 33 to generate the electrical power (Steps 121 & 105 in FIG. 14). The generated electricity is then converted and adjusted to a constant voltage output current by the generator circuit 36 (Step 122 in FIG. 14). The wire (omitted in the drawings) on the first rubber tube 25 delivers the generated electrical power to the display device 44.

Figure 10C:
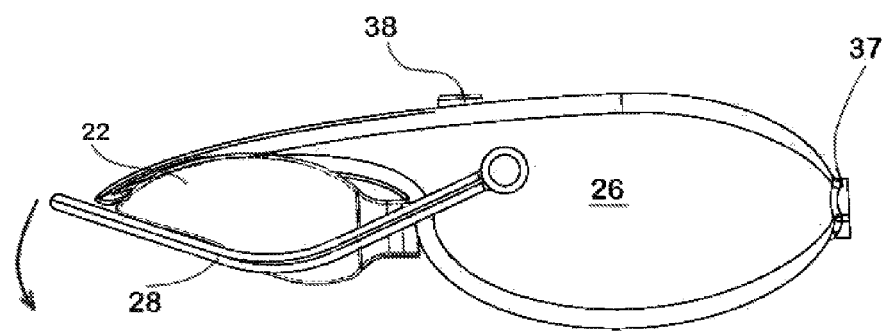
FIG. 10C illustrates a right view of the inflation-power unit portion of the blood pressure monitor according to the first embodiment of the present invention where the operating handle is moving down and the airbag is restoring.
Figure 10D:
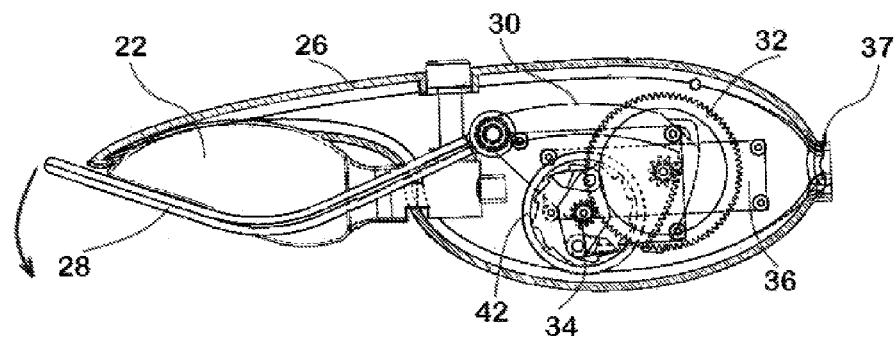
FIG. 10D illustrates a right sectional view of the inflation-power unit portion of the blood pressure monitor according to the first embodiment of the present invention where the operating handle is moving down and the airbag is restoring.

When the operating handle 28 is released after being pushed upward, it will pivot downward in the direction indicated by the arrow in FIG. 10C-D due to the elasticity of the airbag 22, thereby rotating the double gear 32 and the motor gear 34 in a reverse direction by the tooth-bearing rack 30. However, the double gear 32 and the motor gear 34 will rotate idle in the reverse direction and do not drive the generator 42, because the ratchet teeth of the generator 42 are prevented from rotating in reverse by the two pawls 33. After being pushed back to its starting position, the operating handle 28 can be pushed upward again to generate electricity and inflate the cuff 40.

By repeatedly compressing the airbag 22 via the operating handle 28, air is supplied to the inside of the cuff 40. The pressure inside the cuff 40 is measured by the pressure sensor (omitted from the drawings) and displayed on the display device 44. When the pressure reaches a certain value deemed proper for operation of the BP monitor 100, inflation can be halted. Before the cuff 40 is fully inflated, the generator 42 has already generated enough electrical power for the subsequent signal processing and display processes performed by the display device 44 (Step 105 in FIG. 14).

Next, the air is released via pressing and opening the air releasing valve 38 (Step 106 in FIG. 14). Specifically, the air in the cuff 40 passes through the second rubber tube 24, the display device 44, the first rubber tube 25, the air outlet 37 and the air-conducting tube (omitted in the drawings) of the inflation-power unit 23, and is fed to the air releasing valve 38. The air is then bled through the air releasing valve 38 at a desired rate controlled by the thumb of the hand 31.

Simultaneously the air pressure (from which a blood pressure signal is collected) in the cuff 40 is transmitted to the pressure sensor through the second rubber tube 24 so that the air pressure is detected by the pressure sensor and transformed into electrical signals (Step 107 in FIG. 14). The standard signal processing and display circuit will process the signals and generate a set of systolic and diastolic BP values (or BP measurements) of the patient whose blood pressure is being measured. Subsequently the liquid crystal display device will receive and display the BP values on the surface of the display device 44 (Step 108 in FIG. 14). After this, the generated power does not immediately run out and there is still some power left. The leftover power is able to sustain and display the BP values on the display device 44 for a couple of more minutes.

When the BP measurement process is totally done, the air-releasing valve 38 will be fully opened and the air in the cuff 40 is rapidly discharged form the air-releasing valve 38 to end the process (Step 109 in FIG. 14).

FIGS. 11A-C, and 12

Additional Embodiments

In other embodiments of the invention, the blood pressure monitor may have any desired structural means located inside of the airbag (the inflation bulb) for driving the generator.

Figure 11A:
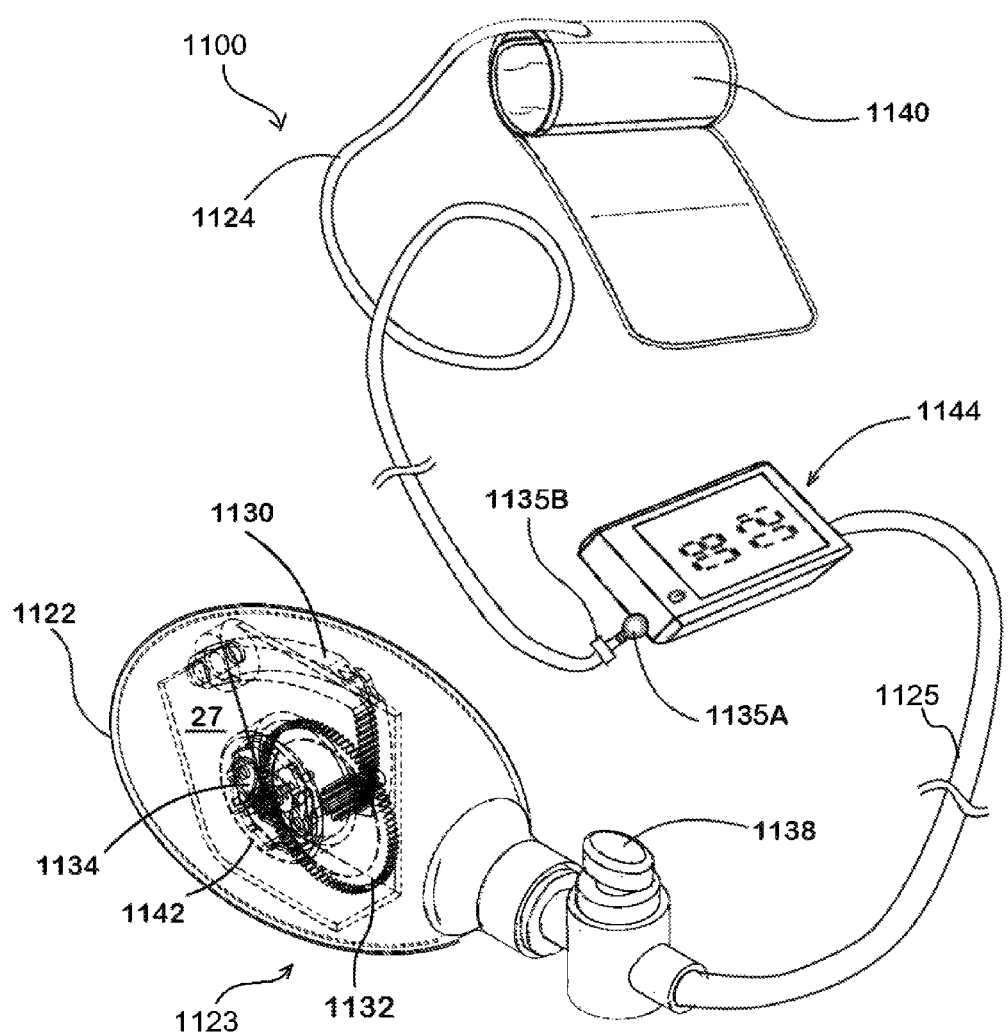
FIG. 11A is a schematic of an overall configuration of a blood pressure monitor according to the second embodiment of the present invention.

FIG. 11A is a schematic of a complete BP monitor 1100 according to the second embodiment of the present invention. The BP monitor 1100 according to the second embodiment differs from that in the first embodiment in that a plurality of the structural means for driving the generator are located inside of the airbag and make contact with its inner surface. The inside structural means may be partially or totally enclosed within the airbag. Basic configurations of a cuff, a display device, a first rubber tube, a second rubber tube connecting the cuff, a display device, an inflation-power unit and the like are identical to those in the first embodiment, omitting explanation thereof.

Figure 11B:
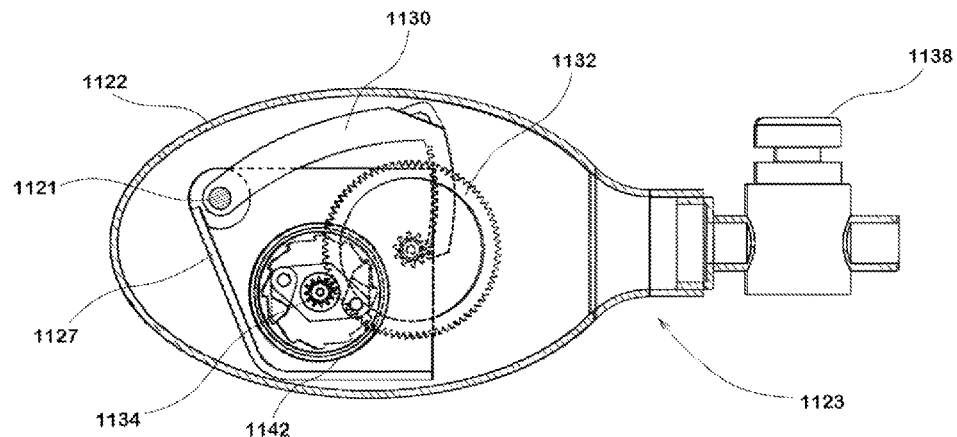
FIG. 11B illustrates a partial sectional side view of an inflation-power unit portion of the blood pressure monitor according to the second embodiment of the present invention.
Figure 11C:
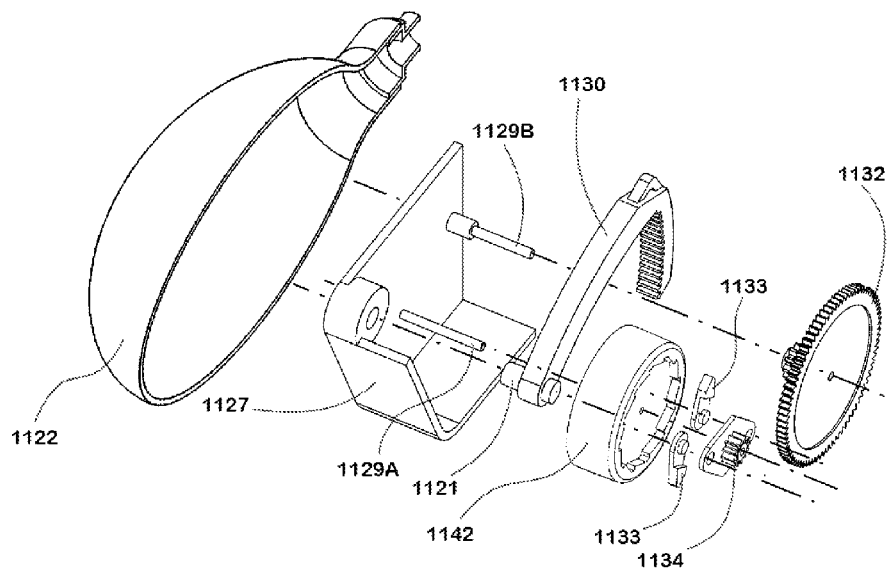
FIG. 11C illustrates a top rearward exploded view of part of the inflation-power unit portion of the blood pressure monitor according to the second embodiment of the present invention.

As shown in FIGS. 11A-C, the BP monitor 1100 includes a cuff 1140 to be applied to an arm (omitted from the drawing), a display device 1144, an inflation-power unit 1123, a first rubber tube 1125 connecting the display device 1144 and the inflation-power unit 1123, and a second rubber tube 1124 connecting the cuff 1140 and the display device 1144.

An open state of the inflation-power unit 1123 is shown in FIG. 11C with the air-releasing valve 1138 omitted. The inflation-power unit 1123 comprises an airbag 1122, an air-releasing valve 1138, a generator 1142, a double gear 1132 and a tooth-bearing rack or a rack 1130, an inside frame 1127 with a first shaft 1129A and a second shaft 1129B. Mounted in the airbag 1122 are the generator 1142, the double gear 1132 and tooth-bearing rack 1130, all of which are fixed on an inside frame 1127 through a fulcrum shaft 1121, a first shaft 1129A and a second shaft 1129B. Specifically the inside frame 1127 has three walls who are contacting each other perpendicularly and form a housing for the generator 1142, the gear transmission unit 1133 and the tooth-bearing rack 1130. The fulcrum shaft 1121 fixes the tooth-bearing rack 1130 to the inside frame 1127, while the first shaft 1129A fixes the generator 1142 and the second shaft 1129B fixes the double gear 1132. The tooth-bearing rack 1130 and the inside frame 1127 are attached to the wall of the airbag 1122 via a attaching means (omitted in the drawings) and allowed to take many orientations inside of the airbag 1122 as long as the tooth-bearing rack 1130 is facing the side wall of the airbag 1122.

The tooth-bearing rack 1130 is a structure taking a general shape of the number "7" and has two ends, where one end is the stalk of the number "7" which is fixed on the fulcrum shaft 1121 while the other end is the top beam part of the number "7" which is placed vertically and has a plurality of teeth meshing with the small diameter teeth of the double gear 1132. Therefore, when the tooth-bearing rack 1130 is pivoting about the fulcrum shaft 1121, the tooth-bearing rack 1130 is driving the double gear 1132 and making the large diameter teeth of the double gear 1132 turn.

The large diameter teeth of the double gear 1132 are again meshing with the motor gear 1134 which is driving the generator 1142 for generation of electricity. The motor gear 1134 is fixated with the generator 1142 via two pieces of pawl 1133. Consequently, the movement of the operating handle 1128 is able to be transmitted to the generator 1142 for electricity generation.

The display device 1144 comprises a pressure sensor (omitted in the drawings) for sensing the pressure in the cuff 1140 delivered via the second rubber tube 1124 and producing BP signals, a standard signal processing and display circuit (omitted from the drawings) for processing the BP signals received and generating and outputting BP values, and a liquid crystal display device (omitted from the drawings) on its surface for receiving and displaying the BP values. In this way, the display device 1144 can automatically receive and process the BP signals the cuff 1140 and have the systolic and diastolic BP values displayed on its surface. The pressure sensor and the standard signal processing and display circuit form a electronic blood pressure measurement unit for receiving the electrical power output from the power generation unit and processing a blood pressure signal from the cuff generating and outputting the BP values; the liquid crystal display device forms a display element for receiving and displaying the BP values. The design and installation of the display device 1144 should be within the knowledge of an artisan in the trade. The design is identical to the display device 44 in the BP monitor 100 of the first embodiment, omitting explanation thereof.

The operation of this embodiment of the present invention differs from that in the first embodiment in that a limb of a human body or an external mechanical device directly deforms the airbag 1122 via squeezing, clenching, compressing or pushing. The inward movement of the wall of the airbag 1122 is coupled with a sliding movement of the tooth-bearing rack 30, which drives the generator 1142 to generate electrical power via the double gear 1132, the motor gear 1134 and two pawls 1133.

When the tooth-bearing rack 1130 is released after being pushed inward, it will then be pushed outward by elasticity of the airbag 1122 due to its attachment with the wall of the airbag 1122. In order for the tooth-bearing rack 1130 to quickly restore to its original position, an individual elastic member (omitted in the drawings) can be added around the fulcrum shaft 1121. The upward restoring movement of the tooth-bearing rack 1130 rotates the double gear 1134 and the motor gear 1134 in a reverse direction. However, the ratchet teeth of the generator 1142 are prevented from rotating in reverse by the pawls 1133 so that the double gear 1132 and the motor gear 1134 will rotate idle in the reverse direction without moving the generator 1142. After restoring to the original position, the airbag 1122 and the tooth-bearing rack 1130 can be squeezed again to generate electricity and inflate the cuff 1140.

By repetition of these movements of the airbag 1122 and the tooth-bearing rack 1130, the air is supplied to the inside of the cuff 1140 while enough electricity power is generated to measure and display the BP values on the display device 1144.

In this particular embodiment, the structural means and the generator are located inside of the airbag 1122, making the blood measure monitor 1100 more compact and easier to store and carry.

In other embodiments of the invention, the blood pressure monitor may have any desired structural means adapted for a part of a foot to fit in, making the measuring process more convenient for people with disabled hands.

Figure 12:
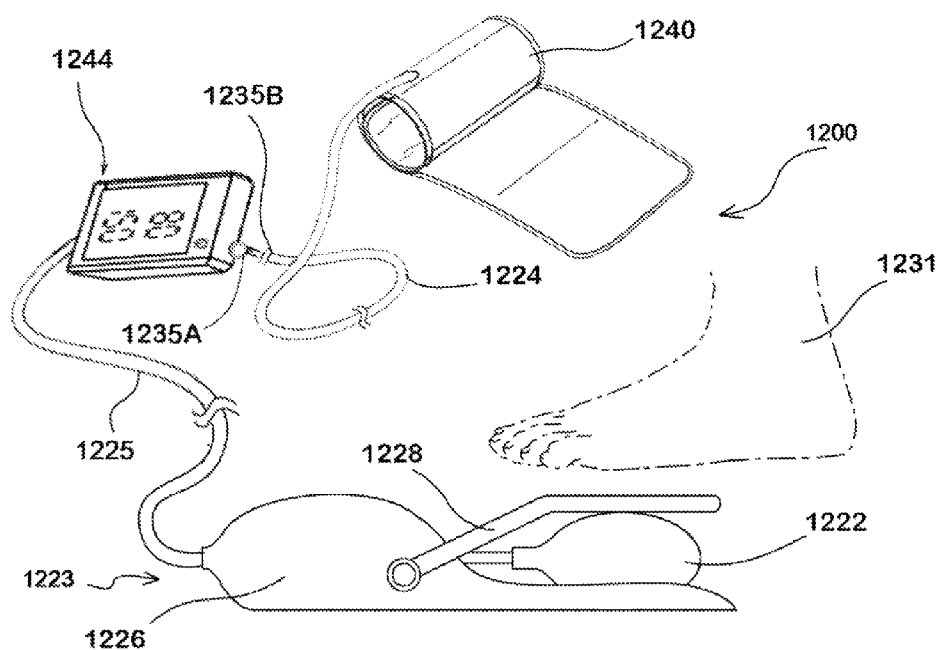
FIG. 12 is a schematic of an overall configuration of a blood pressure monitor according to the third embodiment of the present invention.

FIG. 12 is a schematic of an overall BP monitor 1200 according to the third embodiment of the present invention. The BP monitor 1200 according to the third embodiment differs from that in the first embodiment in that the inflation-power unit is adapted for a foot to operate and has the operating handle facing upwards in a flat-topped configuration. Basic configurations and functions of a cuff, a display device, a first rubber tube, a second rubber tube to connect the cuff, a display device, an inflation-power unit and the like are identical to those in the first embodiment, omitting explanation thereof.

As shown in FIG. 12, the BP monitor 1200 includes a main body made up of a display device 1244 and an inflation-power unit 1223 being joined through a first rubber tube 1225, and a cuff 1240 to be applied to an arm (omitted from the drawing) and connected with the main body by a second rubber tube 1224. The main body also has an air-releasing valve (omitted in the drawing) connected with both the display device 1244 and the inflation-power unit 1223 through the first rubber tube 1225 to release the air from the cuff 1240 in the process. The first rubber tube 1225 has a wire (omitted in the drawings) to conduct the electrical power generated from the inflation-power unit 1223 to the display device 1244. The display device 1244 is identical to the display device 44 in the BP monitor 100 of the first embodiment, where BP signals are sensed and processed, and the systolic and diastolic BP values are displayed.

Some parts of the inflation-power unit 1223 can be advantageously laid on the ground (omitted in the drawings) and operated by a foot 1231. Besides the air-releasing valve (omitted in the drawing), three parts of the external configuration of the inflation-power unit 1223 can be seen in FIG. 12, including a casing 1226 touching the ground, an operating handle 1228 which is flat-topped for placing the foot 1231, and an airbag 1222 securely sandwiched in the space between the casing 1226 and the operating handle 1228. The casing 1226 on the ground has a form like a tadpole in the recumbent position, with a head and a tail. The ultimate end of the head of the casing 1226 is connected to the display device 1244 via the first rubber tuber 1225 for transmitting the air and the electrical power. The operating handle 1228 pairs with the tail of the casing 1226 to sandwich the airbag 1222. The operating handle 1228 is a forklike structure having two ends: one end is pivotally connected to the casing 1226 with a fulcrum shaft (omitted in the drawings) while the other end is configured to hold part of the airbag 1222. The operating handle 1228 can pivotally move up and down during the inflation and electricity generation process. The head of the casing 1226 houses a tooth-bearing rack connected to a fulcrum shaft, a double gear, a motor gear, a generator, a generator circuit and the like, which are identical to those in the first embodiment, omitting explanation thereof.

The operation of the embodiment of the present invention is identical to those in the first embodiment, except that the inflation-power unit 1223 is laid on the ground and operated with the foot 1231 via stomping or stepping. Since the foot 1231 usually is more forceful than a hand, the BP monitor 1200 can have advantages such as quicker inflation and electrical power generation. In addition, this embodiment of the BP monitor 1200 requires only one foot for most of the BP measuring, so it is especially advantageous for patients with disabilities of the hands.

FIGS. 13A-C

Modifications and Alternative Embodiments

Figure 13A:
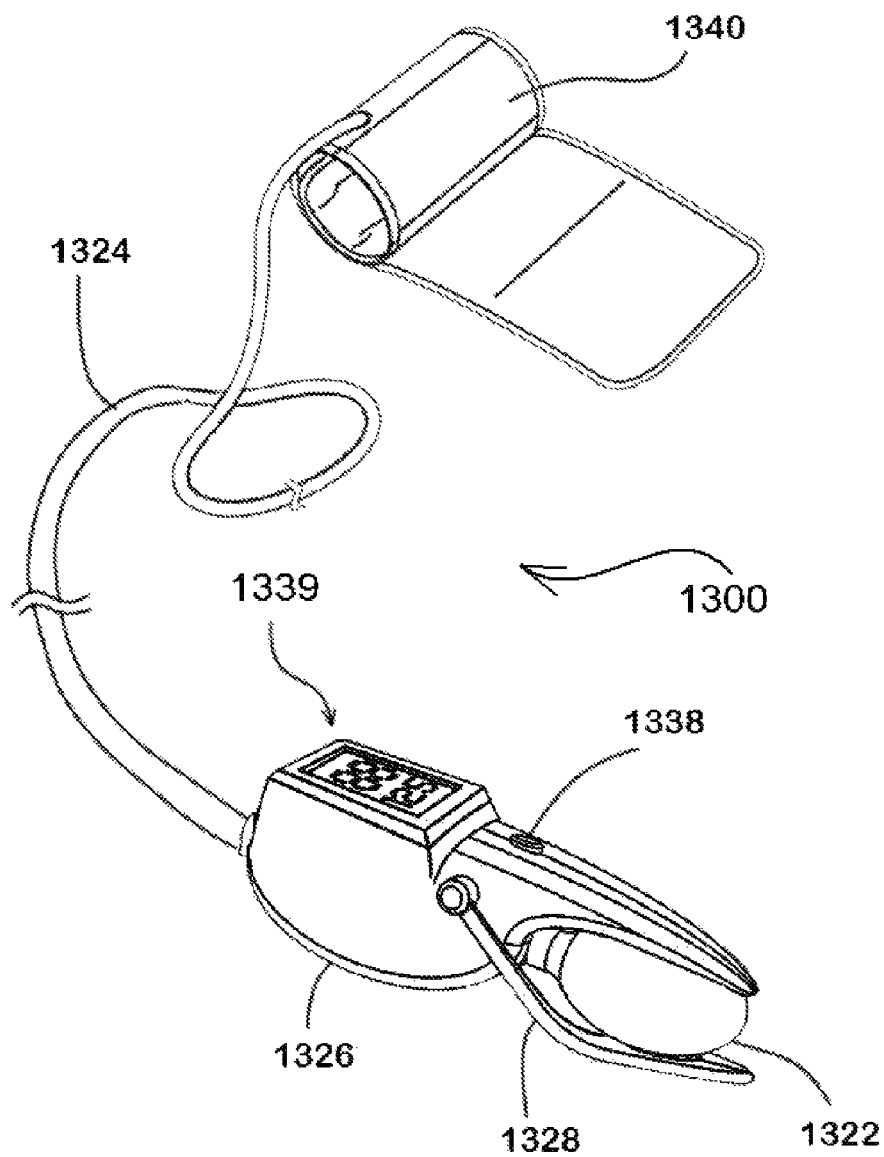
FIG. 13A is a schematic of an overall configuration of a blood pressure monitor according to the fourth embodiment of the present invention.
Figure 13B:
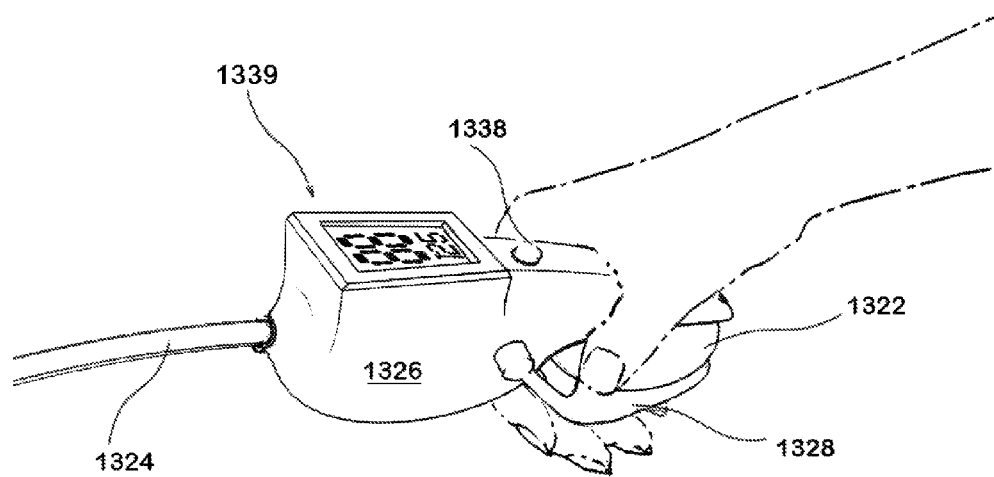
FIG. 13B is a perspective view of a main body portion of the blood pressure monitor according to the fourth embodiment of the present invention.
Figure 13C:
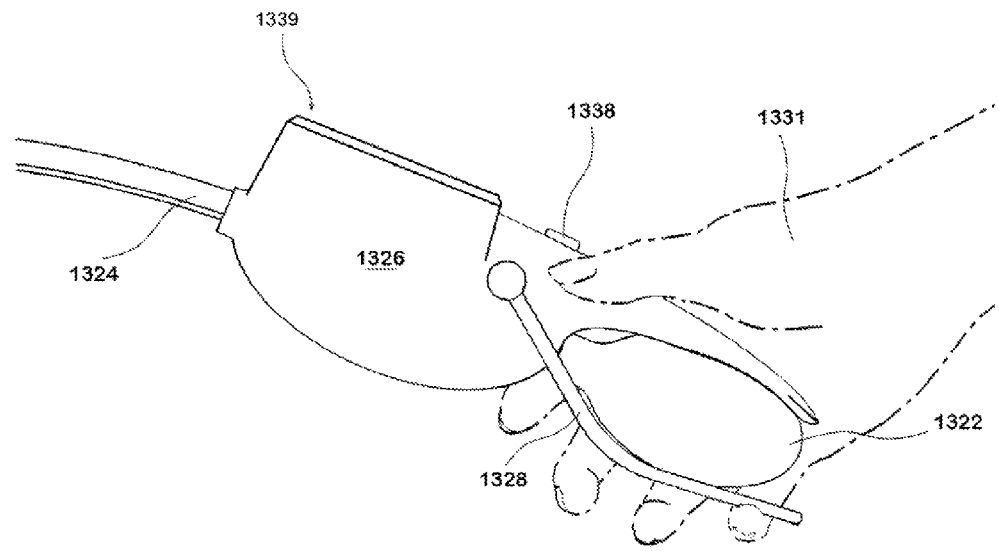
FIG. 13C is a perspective view of the main body portion of the blood pressure monitor according to the fourth embodiment of the present invention.

There are various possibilities with regard to the relative disposition of the display device where mounted are the liquid crystal display on the surface and the standard signal processing and display circuit (omitted from the drawings) for processing the electronic signals received and displaying the BP values. FIG. 13 illustrates an overall configuration of an embodiment of the present invention. A BP monitor 1300 includes a cuff 1340 to be applied to an arm (omitted from the drawing), and a main body 1339 connected to the cuff 1340 via a rubber tube 1324.

The main body 1339 basically has all inner parts of the display device 44 and the inflation-power unit 23 previously shown in FIGS. 5-6, mounted in a single casing 1326. Specifically, the main body 1339 comprises the casing 1326, a liquid crystal display device for displaying a BP measurement reading on the surface of the main body 1339, an airbag 1322 to inflate the cuff 1340, an air-conducting unit (omitted in the drawings) to conduct the air between the airbag 1322 and the cuff 1340 (the air-conducting unit includes an air-releasing valve 1338 for releasing air during the process), an operating handle 1328 pairing with part of the casing 1326 to confine the airbag 1322, a tooth-bearing rack (omitted in the drawings) pivotally connected with the operating handle 1328 via a fulcrum shaft (omitted in the drawings), a double gear (omitted in the drawings) to connect with the tooth-bearing rack, a generator (omitted in the drawings) driven by the double gear, a generator circuit (omitted in the drawings) to regulate the electrical current from the generator, a pressure sensor (omitted in the drawings) to sense the air pressure in the cuff 1340 delivered via the rubber tube 1324 and produce electronic BP signals, a standard signal processing and display circuit (omitted from the drawings) for processing the BP signals received and generating and outputting BP values, and a liquid crystal display device (omitted from the drawings) on its surface for receiving and displaying the BP values. The signal processing and display circuit and the generator circuit are identical to the ones in the BP monitor 100 of the first embodiment. The rubber tube 1324 directly plugs into the main body 1339.

The operation of the BP monitor 1300 is identical to the BP monitor 100 of the first embodiment of the present invention. Among many advantages for the embodiment, it has a compact design and is easier for the operator to see the BP results. Additionally, it might also have a lower cost of manufacture due to having only one integration piece for the main body.

The modification which combines the display unit and the inflation-power unit into one piece of the main body is compatible with other features of the present invention and most other embodiments of the present invention.

Additionally, a BP monitor embodying the principles of the invention can have any desired structure of the operating handle and the rack. For example, the operating handle 28 and the tooth-bearing rack 30 can be a single integrated piece (omitted in the drawings) and be incorporated in all embodiments of the invention. The integrated piece (omitted in the drawings) has a central portion and two ends. The central portion of the integrated piece is pivotally connected to the fulcrum shaft 43 and is able to turn around the fulcrum shaft 43. The fulcrum shaft 43 is securely fixed to the casing 26. One end of the integrated piece is mounted in the casing 26 and engaged with the double gear 32 while the other end extends out of the casing 26 and pairs with the tail part of the casing 26, securely holding the airbag 22 in place. The very end of the inside part of the integrated piece is extending down towards the belly of the casing 26, and has a plurality of teeth meshing with the small diameter teeth of the double gear 32. The modification of the operating handle 28 and the tooth-bearing rack 30 is workable with all embodiments of the present invention.

In one or more embodiments according to this invention, more than one bulb or airbag can be used: some of them can be primarily for electricity generation while others primarily for cuff inflation.

In one or more embodiments according to this invention, the inward movement of the wall of the airbag during inflation is operably coupled to produce electricity. However, the outward movement of the wall of said elastic airbag during inflation can be operably coupled to produce electricity too.

In one or more embodiments according to this invention, the airbag is elastic so that the handle or the tooth-bearing rack to restore to its original position. The airbag, however, can be non-elastic. At least one elastic member, such as one or more springs (omitted in the drawings) can be included in the inflation-power unit, in order for the handle or the tooth-bearing rack or the airbag to quickly restore to its original position (referring, for example, to the tooth-bearing rack 30 in the BP monitor 100 or the tooth-bearing rack 1130 in the BP monitor 1100).

In one or more embodiments according to this invention, the generator is a typical generator with an electromagnetic coil, but it can be any other type of generator that provides the functionality and compatibility envisioned in the one or more of the embodiments of the invention. Furthermore, the generator can be comprised of a plurality of two or more different types of electromechanical generators and/or generators that provide similar or different efficiencies and modes of energy generation to supply the energy requirements disclosed and envisioned in the one or more embodiments of the current invention.

In one or more embodiments according to this invention, the liquid crystal display device can be replaced/coexisting with one or more devices capable of transmitting the BP measurement of the patient to at least one destination, such as a user, a database, a dataset, a computer readable memory, a computer readable medium, a computer processor, a computer network, a printout device, a visual display, and a wireless receiver.

In one or more embodiments according to this invention, a plurality of rechargeable batteries and/or other types of energy storage devices can be included to store the electrical power generated by the generator. However, in other embodiments of the current invention, the power storage devices and/or the voltage regulator devices may be omitted from the BP monitor device.

Each of these details provides particular advantages and can be implemented independently of the others.

If desired, some control devices (omitted in the drawings) can be optionally included to decouple the inflation and the electricity generation processes for a length of time. The control devices can include, but are not limited to, buttons, control circuits, switches and other electromechanical devices. The installation and operation of the control device as well as all above modifications should be within the knowledge of an artisan in the trade. Embodiments of the invention which incorporate the additional control device can be used to generate the electrical power first, and the electrical power generated can then be used to inflate the arm-banding cuff and measure and display the BP values of the patient.

DETAILED DESCRIPTION

Advantages

From the description above, a number of advantages of our BP monitors become evident:

(a) No battery or external power supply electricity is needed. Our BP monitors are care-free and require minimal maintenance. They are always ready for immediate use under any conditions, particularly urgent circumstances such as following disasters, or in outdoor environments. Our BP monitors can be pulled out and used right away without the need to fumble around for batteries or other forms of power supply, which could be rather stressful and very inconvenient in such situations.

(b) No waiting period is needed for use of our BP monitors. Enough electrical power is generated with a few strokes of squeezing the airbag, which can sustain the whole BP measurement process and display the BP values for at least a couple of minutes.

(c) The cost to manufacture is low since the building materials of our BP monitors are common and readily available, thus avoiding the material requirement for solar panels or wind power generators as in the prior art.

(d) The compact and ergonomic designs of our BP monitors make their storage and usage quite simple. They don't contain batteries or mercury so there is no worry about battery leakage or mercury spillage. The measurement is automatic and almost any patient can operate it with little or no help from others.

Conclusion and Scope

Accordingly, the reader will see that the battery-free BP monitor of this invention can be stored easily and, in a maintenance-free style, can be started to measure systolic and diastolic pressure immediately. It can be used conveniently and independently without help from other people, and is easy to manufacture.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

As used herein, the phrase "power generation unit" refers to a functional unit of a plurality of parts in the inflation-power unit for electrical power generation. shown in one or more embodiments of the invention The phrase "electrical generator" refers to a generator shown one or more embodiments of the invention.

What is claimed is:

1. A manually-driven battery-free electronic blood pressure measuring apparatus, comprising:
   a) a cuff;
   b) an airbag to inflate the cuff;
   c) a power generation unit for generating and outputting electrical power, wherein the power generation unit is comprised of i) an electrical generator and ii) a manual generator-driving means operably coupled to the wall of said airbag; and
   d) an electronic blood pressure measurement unit for receiving the electrical power output from the power generation unit and processing a blood pressure signal from the cuff;
   wherein the manual electrical generator-driving means is a rack, the rack being capable of attaching to the inner surface of the airbag, wherein the rack is mounted in the airbag, wherein the electrical generator is mounted in the airbag.

* * * * *